United States Patent
Nogawa et al.

(10) Patent No.: US 7,300,628 B2
(45) Date of Patent: Nov. 27, 2007

(54) AUTOMATIC ANALYZING APPARATUS

(75) Inventors: Keiko Nogawa, Hitachinaka (JP); Michiaki Sekiguchi, Mito (JP); Hiroshi Watanabe, Hitachinaka (JP); Hiroaki Ishizawa, Hitachinaka (JP); Terumi Tamura, Hitachinaka (JP)

(73) Assignee: Hitachi High-Technologies Corporation, Tokyo (JP)

(*) Notice: Subject to any disclaimer, the term of this patent is extended or adjusted under 35 U.S.C. 154(b) by 739 days.

(21) Appl. No.: 10/445,918

(22) Filed: May 28, 2003

(65) Prior Publication Data

US 2003/0235514 A1 Dec. 25, 2003

(30) Foreign Application Priority Data

May 29, 2002 (JP) ............................. 2002-154898

(51) Int. Cl.
*B32B 5/02* (2006.01)
*G01N 35/02* (2006.01)
*B32B 27/12* (2006.01)

(52) U.S. Cl. ..................... 422/65; 422/67; 436/48; 436/50

(58) Field of Classification Search ............ 422/64, 422/65
See application file for complete search history.

(56) References Cited

U.S. PATENT DOCUMENTS 6,117,392 A * 9/2000 Hanawa et al. ............... 422/65

FOREIGN PATENT DOCUMENTS

JP 10-213586 8/1998

* cited by examiner

*Primary Examiner*—Jill Warden
*Assistant Examiner*—Neil Turk
(74) *Attorney, Agent, or Firm*—Mattingly, Stanger, Malur & Brundidge, P.C.

(57) ABSTRACT

An automatic analyzing apparatus has an analysis section including an immunity analysis unit and a biochemical componential analysis unit. A sample rack which has undergone the immunity componential analysis is horizontally fed by a rack feeding mechanism from a position confronting the inlet of a rack stationing section to a position near the outlet of the rack stationing section, so that the sample rack is directly moved to a return line, while skipping over the rack stationing section, so as to be efficiently returned to the analysis section and subjected to a subsequent biochemical analysis. A sample rack that needs reexamination by an identical analysis unit is also returned in the same efficient way.

4 Claims, 5 Drawing Sheets

⇨ MOTION OF 1ST RACK SORTING MECHANISM
⇛ MOTION OF 2ND RACK SORTING MECHANISM

⇨ MOTION OF 1ST RACK SORTING MECHANISM

⇨ MOTION OF 2ND RACK SORTING MECHANISM

⇨ MOTION OF 1ST RACK SORTING MECHANISM

⇨ MOTION OF 2ND RACK SORTING MECHANISM

AUTOMATIC ANALYZING APPARATUS

BACKGROUND OF THE INVENTION

1. Field of the Invention

The present invention broadly relates to an automatic analyzing apparatus which automatically performs componential analysis of samples such as blood or urine that are extracted from living bodies and, more particularly, to an automatic analyzing apparatus which shifts samples from sample vessels in a sample rack into an analyzing section for analysis, and which performs reexamination as required.

2. Description of the Related Art

Automatic analyzing apparatuses of the kind described are capable of quickly analyzing a lot of samples extracted from living bodies and, therefore, are widely used in medical centers and clinical examination centers. On the other hand, there is an increasing demand for further increase of the throughput per unit time and further diversification of analysis items. In order to cope with demand, a module-type analyzing apparatus has been proposed which incorporates a plurality of analyzing modules connected to a transfer line which transfers sample racks accommodating sample vessels. Another type of automatic analyzing apparatus has also been proposed which has a mechanism for shifting a selected sample rack back to the inlet or upstream end of the transfer line through a return line, for the purpose of reexamination which is necessary when, for example, the density of the samples failed to fall within the range measurable by the apparatus. This type of automatic analyzing apparatus has been disclosed in and known from JP-A-10-213586.

SUMMARY OF THE INVENTION

In the automatic analyzing apparatus disclosed in JP-A-10-213586, sample racks containing matters which need not be re-examined, e.g., a control sample, a standard sample, and a cleaning fluid, are registered at a control section of the apparatus as being non-reexamination sample racks that need not be subjected to reexamination. A non-reexamination rack upon reaching the terminal end of the transfer line is directed to a rack collecting section, by means of a first sorting unit which is installed at the terminal end of the transfer line, whereas other sample racks containing sample samples are all directed to a rack stationing section composed of a U-shaped line. A second sorting unit, which is installed downstream of the first sorting unit, operates to select sample racks to be subjected to reexamination out of the racks that are stationed in the rack stationing section and directs the selected sample racks to the return line, while directing other racks that need not be reexamined to the rack collecting section.

Thus, sample racks that were determined before reaching the first sorting unit as being unnecessary to be reexamined are also temporarily stationed in the rack stationing section.

When the automatic analyzing apparatus employs a biochemical analyzer alone connected to the transfer line, probability of occurrence of the need for reexamination is quite low, so that the above-described arrangement is usable without substantial risk of trouble. This, however, is not true with an automatic analyzing apparatus of the type which employs both an automatic immunity analyzer and an automatic biochemical analyzer that are connected to an identical transfer line. More specifically, this type of automatic analyzing apparatus tends to suffer from impairment of reliability due to carry-over, i.e., contamination of a sample with another kind of sample, which may occur through the use of a dispensation device. One solution to this problem is to conduct an immunity analysis prior to biochemical analysis. This solution, however, tends to cause a delay in the finalization of the examination report because all the sample racks having vessels containing samples are temporarily stationed at the rack stationing section.

It is also to be noted that the total analyzing time may considerably shortened even in the case of the automatic analyzing apparatus of the type which employs either one of the immunity analyzer or the biochemical analyzer, if the apparatus is arranged such that the sample racks, which have been determined before reaching the first sorting unit as being not necessary to be reexamined, are directly sent to the rack stationing section.

Accordingly, it is an object of the present invention to provide an automatic analyzing apparatus with which automatic analysis can be conducted in a shorter time than by known apparatuses.

To this end, in accordance with one aspect of the present invention, there is provided an automatic analyzing apparatus, comprising: an analysis section for examining samples extracted from sample vessels accommodated in sample racks; a transfer line for transfering the sample racks to the analysis section and for further transfering the sample racks to an outlet after the extraction of the samples; a rack supplying section for supplying the sample racks to the transfer line; a rack stationing section for stationing sample racks which have possibility of being subjected to a reexamination; a rack collecting section for accommodating the sample racks with which the examination has been finished; a return line along which the sample racks that need to be reexamined back to the analysis section; a first rack sorting section for receiving the sample racks transfered by the transfer line, the first rack sorting section directing sample racks that have to await determination as to the necessity for the reexamination to the stationing section, while directing sample racks that do not have to await the determination to a second rack sorting section; wherein the second rack sorting section selects, from among the sample racks which have been received from the first rack sorting section and which need not await the determination, a sample rack determined as necessitating the reexamination and directing the selected sample rack to the return line, while directing the sample racks with which the examination has been finished to the rack collecting section, the second rack sorting section also directing a sample rack that needs to be reexamined from among the sample racks which have been stationed in the stationing section to the return line, while directing sample racks that need not be reexamined to the rack collecting section.

In accordance with another aspect of the present invention, there is provided an automatic analyzing apparatus, comprising: an analysis section for examining samples extracted from sample vessels accommodated in sample racks; a transfer line for transfering the sample racks to the analysis section and for further transfering the sample racks to an outlet after the extraction of the samples; a rack supplying section for supplying the sample racks to the transfer line; a rack stationing section for stationing sample racks which have possibility of being subjected to a reexamination; a rack collecting section for accommodating the sample racks with which the examination has been finished; a return line along which the sample racks that need to be reexamined back to the analysis section; a first rack sorting section for receiving the sample racks transfered by the transfer line, the first rack sorting section directing sample racks that have to await determination as to the necessity for the reexamination to the stationing section, and selecting, from among the sample racks that need not await the determination, sample racks that do not need the reexamination and directing the selected sample racks to the collecting section, while directing the sample racks that need the reexamination to a second rack sorting section; wherein the second rack sorting section directs the sample racks that need the reexamination received from the first rack sorting section to the returning line, the second rack sorting section also selecting, from among the sample racks stationed in the stationing section, sample racks that need the reexamination and directing the selected sample racks to the return line, while directing the sample racks that do not need the reexamination to the collecting section.

In accordance with still another aspect of the present invention, there is provided an automatic analyzing apparatus, comprising: an analysis section for examining samples extracted from sample vessels accommodated in sample racks; a transfer line for transfering the sample racks to the analysis section and for further transfering the sample racks to an outlet after the extraction of the samples; a rack supplying section for supplying the sample racks to the transfer line; a rack stationing section for stationing sample racks which have possibility of being subjected to a reexamination; a rack collecting section for accommodating the sample racks with which the examination has been finished; a return line along which the sample racks that need to be reexamined back to the analysis section; a first rack sorting section for receiving the sample racks transfered by the transfer line, the first rack sorting section directing sample racks that have to await determination as to the necessity for the reexamination to the stationing section, while directing sample racks that need the reexamination to the return line and directing sample racks that do not need the reexamination to the rack collecting section; and a second rack sorting section for selecting, from among the sample racks stationed in the stationing section, sample racks that need the reexamination and directing the selected sample racks to the return line, while directing the sample racks that do not need the reexamination to the collecting section.

The described arrangements are particularly suitable for an automatic analyzing apparatus of the type which has both an automatic immunity analysis section and an automatic biochemical analysis section which are connected to a common transfer line, wherein the automatic immunity analyzing section performs an immunity componential analysis for determining whether a specific antigen or a specific antibody is contained in a sample, i.e., a sample, while the automatic biochemical analysis section which performs a biochemical componential analysis.

The present invention, when incorporated in this type of automatic analyzing apparatus, permits the samples after the immunity analysis to be quickly sent for the subsequent biochemical analysis through the return line while skipping over the stationing section, thus contributing to the shortening of the total analytic processing time.

Preferably, each of the automatic analyzing apparatuses described heretofore further comprises a registration section in which information as to the necessity for the reexamination for each sample rack has been registered; and a control section for controlling the operation of the rack sorting sections in accordance with the registered information.

The stationing section may be configured to have a receiving area for receiving the sample racks from the inlet of the stationing section and a delivery area through which the sample racks are delivered to the outlet of the stationing section after lapse of a stationing period, the receiving area and the delivery area being arranged to provide a substantially U-shaped path of transfer of the sample racks.

The above and other objects, features and advantages of the present invention will become clear from the following description of the preferred embodiments taken in conjunction with the accompanying drawings.

DESCRIPTION OF THE PREFERRED EMBODIMENTS

Figure 1:
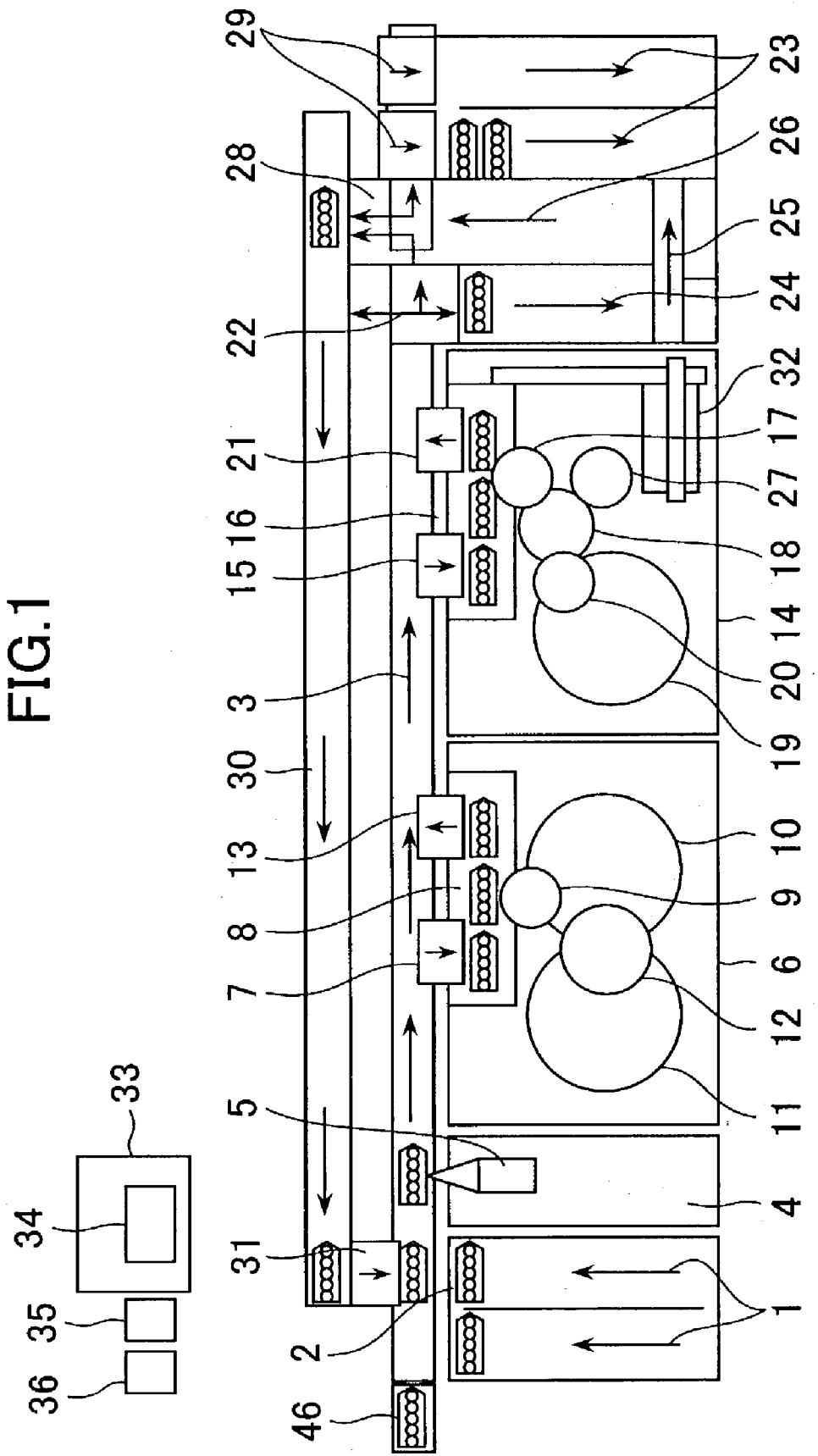
FIG. 1 is a schematic illustration of the general arrangement of an automatic analyzing apparatus embodying the present invention.

FIG. 1 shows general arrangement of an automatic analyzing apparatus which is an embodiment of the present invention. This automatic analyzing apparatus is of the type known as a hybrid apparatus which combines both an automatic biochemical analyzer 6 and an automatic immunity analyzer 14. A plurality of sample racks 2 are arrayed in a rack supplying section 1 and are transferred to a transfer line 3. The racks 2 are transferred by the transfer line 3 past a recognition section 4 having a recognition device 5 which may be, for example, a reader for reading identifiers such as bar codes provided on sample vessels accommodated in each sample rack 2, whereby each sample is identified by a rack number and a sample vessel number. The sample rack number and the sample vessel number recognized by the recognition device are transmitted to a control section 33. Analysis instructions including information concerning items of analysis to be performed on the samples in sample vessels in each sample rack 2 have been given from an operating section to the control section 33, in relation to sample receipt numbers. The control section 33 then checks up the sample vessel numbers with the sample receipt numbers to find the kind of analysis item to be performed on the sample vessels, and determines the destination of each sample rack 2 according to the item of the analysis to be performed. The information including the item of the analysis and the destination of the sample racks 2 are stored in a memory section 34 so as to be used in the analytical processing executed on the sample racks 2.

An emergency rack supplying section 46 is provided upstream of the rack supplying section 1. When a sample rack 2 is placed on the emergency rack supplying section 46 while other sample racks are stationed at the rack supplying section 1, the rack 2 on the emergency rack supplying section 46 is transferred to the transfer line 3 in preference to the racks on the rack supplying section 1.

The automatic immunity analyzing section 14, which is arranged along the transfer line 3, has the following components or elements: a sampling area 16 which receives the sample racks 2 from the transfer line 3 and returns the sample racks 2 after a sampling treatment back to the transfer line 3; a reaction disc 18 which allows and promotes a reaction between the sample and a reagent in each of a plurality of reaction vessels arranged along a circle, according to the item of analysis to be performed; a reaction vessel feeding mechanism 32 for feeding independent reaction vessels one by one to the reaction disc; a reagent disk 19 operative to locate each of reagents to be used for a variety of analysis items at a reagent sucking position; a reaction mixture sucking mechanism 27 for introducing the reaction mixture formed as a result of the reaction in each reaction vessel into a measuring unit; a measuring section in which an electrical potential is given to an activating electrode as to cause the reaction mixture to illuminate, and the luminous intensity is measured; a sample dispensation mechanism 17 for dispensing samples from the sample vessels in the sampling area 16 into the reaction vessels in the reaction disc 18; and a reagent dispensation mechanism 20 which dispenses reagents from reagent bottles in the reagent disk 19 into the reaction vessels in the reaction disc 18 according to the items of the analysis to be performed.

The automatic biochemical analyzing section 6 has the following components or elements: a sampling area 8 which receives the sample racks 2 from the transfer line 3 and returns the sample racks 2 after a sampling treatment back to the transfer line 3; a reaction disc 10 which allows and promotes a reaction between the sample and a reagent in each of a plurality of reaction vessels arranged along a circle, according to the item of analysis to be performed; a reagent disk 11 operative to locate each of the reagents to be used for a variety of analysis items at a reagent sucking position; a multi-wavelength spectrophotometer for measuring absorbance of the reaction mixture of the sample and a reagent formed in each reaction vessel; a sample dispensation mechanism 9 for dispensing samples from the sample vessels in the sampling area 8 into the reaction vessels in the reaction disc 10; and a reagent dispensation mechanism 12 which dispenses reagents from reagent bottles in the reagent disk 11 into the reaction vessels in the reaction disc 10 according to the items of the analysis to be performed.

Each sample rack 2 to be subjected to an analytical examination by the automatic immunity analyzing section 14 or by the biochemical analyzing section 6 is shifted from the transfer line 3 to the sampling area 8 or to the sampling area 10, by means of a rack pickup mechanism 7 or a rack pickup mechanism 15. The sample racks 2 thus shifted are moved to a sampling position in the sampling area 8 or the sampling area 16, where dispensation nozzles of the sample dispensation mechanism 9 or the sample dispensation mechanism 17 is inserted into the desired sample vessels, for the dispensation of the sample into the reaction vessels.

After the extraction of the samples for all the analysis items under the analysis instruction, the sample racks 2 are moved to a position where a rack ejection mechanism 13 or a rack ejection mechanism 21 is disposed, and are shifted back onto the transfer line 3 by means of the rack ejection mechanism. Each sample dispensed into the reaction vessel on the reaction disk 10 or the reaction disc 18 is made to react with an agent which is dispensed by the reagent dispensation mechanism 12 or by the reagent dispensation mechanism 20. After elapse of a predetermined time, the measurement is conducted so that measurement data is obtained for each of the analytical items. The analytical measurement data thus obtained is delivered to the control section 33. The control section 33 then checks up the analytical measurement data with a predetermined standard data to confirm whether the analytical measurement data is acceptable. Upon determining that a reexamination is necessary due to failure to meet the standard, the control section 33 operates to inform the memory section 34 of the fact that the reexamination is necessary, together with the information indicating the sample rack number and the sample vessel number with which the failure has been detected. The control section 33 also controls the operation of a later-mentioned rack sorting mechanism 22 at proper timings. Conversely, the sample racks 2 that were determined as being unnecessary to be reexamined are transferred to and accommodated in a rack accommodating section 23. After the measurement is completed, the results are displayed on a display section 36 and are stored in the memory section 34.

Figure 2:
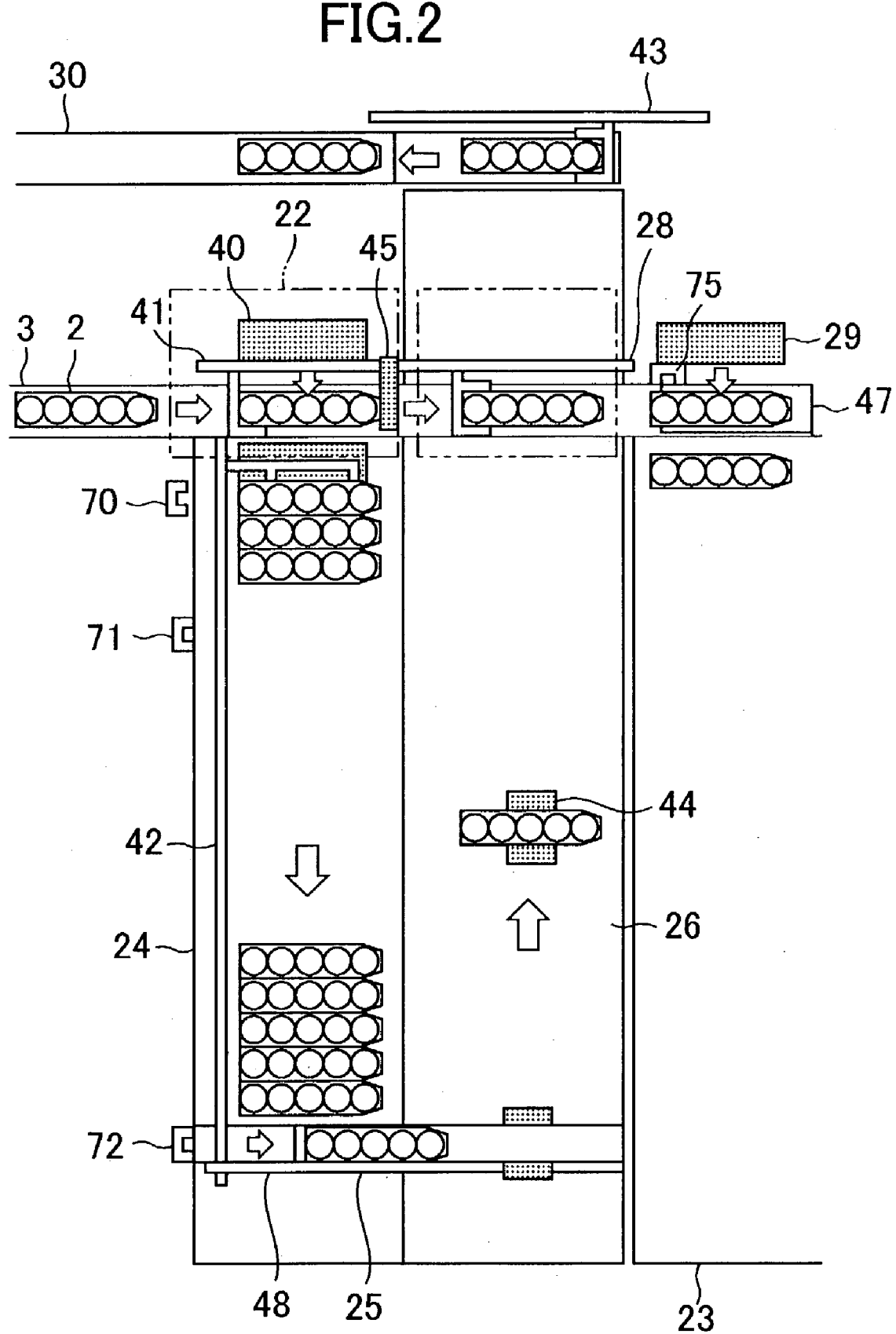
FIG. 2 is an illustration of a portion of a known automatic analyzing apparatus, showing a path along which sample racks are transfered when reexamination is necessary.

A description will now be given of a conventional route or path along which the sample racks to be subjected to reexamination are transferred, with specific reference to FIGS. 1 and 2.

The rack sorting mechanism 22 has the following components: a reciprocal rack pushing mechanism 40 which in its forward stroke pushes the sample rack 2 into a rack stationing section 24; a rack feeding mechanism 41 having claws which are moved by, for example, an endless belt so as to push the trailing ends of the sample racks 2; and a retractable rack stopper 45 having a solenoid-actuated member which when projected abuts the leading end of the sample rack 2 thereby preventing further movement of the sample rack 2. A rack take-up mechanism 28 includes a rack forwarding mechanism which pushes the trailing ends of the sample racks which are carried by a forwarding line 26 and which need not be reexamined, so as to transfer these racks 2 to a belt of an accommodation line 47. A rack return mechanism 43, which is provided at the inlet of a return line 30, has claws that are moved by, for example, an endless belt so as to push the trailing ends of the sample racks 2 which have been forwarded by the forwarding line 26 and which are to be subjected to reexamination, thereby transferring these racks 2 to the return line 30. Sensors for confirming positions of the racks are disposed at suitable positions along the path of transfer of the sample racks.

As explained before in connection with FIG. 1, a decision has been made by the control section 33 as to whether each sample rack 2 on the forwarding line 26 is to be sent to the rack accommodating section 23 or to the rack stationing section 24, before the sample rack 2 reaches the rack sorting section 22.

When the control section 33 has determined that the sample rack 2 is to be sent to the rack accommodating section 23, the retractable rack stopper 45 is kept inoperative. After absence of any rack at the inlet of the rack stationing section 24 has been confirmed by a rack sensor 74, the rack feeding mechanism 41 is activated so as to send the rack 2 to the inlet of the rack stationing section 24. Then, after confirming absence of any rack at the outlet of the rack stationing section 24 by a rack sensor 75, the rack take-up mechanism 28 is activated so that the rack 2 is moved onto the accommodation line 47 past the outlet of the rack stationing section, on condition that absence of any rack on the accommodation line 47 has been confirmed by a rack sensor 77. The rack 2 is then transferred by the accommodation line 47 to the inlet of the rack accommodation section 23, and is pushed by a rack pushing mechanism 29 into the rack accommodation section 23, so as to be stored in the latter.

Conversely, when the control section 33 has determined that the sample rack 2 is to be brought to the rack stationing section 24, the retractable rack stopper 45 is activated so that the sample rack 2 is stopped at the inlet of the rack stationing section 24, and the rack pushing mechanism 40 is activated to push the rack 2 into the rack stationing section 24. Safe receipt of the rack 2 by the rack stationing section 24 is confirmed by a rack sensor 70 which is installed at the inlet of the rack stationing section 24. A plurality of sample racks 2 are thus successively brought into the rack stationing section 24. When no sample rack 2 is brought to the rack sorting mechanism 22 until a rack sensor 71 senses any sample rack or until a predetermined period of time lapses, a batch of the sample racks 2 is fed by a rack feeding mechanism 42 to a rack delivery position 48. After absence of any sample rack on a forwarding arm 44 of the forwarding line 26 is confirmed by a rack sensor 72, a rack shifting mechanism 25 is activated so that the sample racks 2 that have been sent to the rack delivery position are shifted to and grasped by the rack forwarding arm 44. If a determination has been made as to whether the sample rack 2 grasped by the forwarding arm 44 it to be subjected to the reexamination, the sample rack 2 is immediately forwarded to the rack take-up mechanism 28 or to the return line 30. The sample rack 2 when forwarded to the return line 30 is transferred by a rack returning mechanism 31 onto the transfer line, so as to be sent to the analysis section. If the determination as to the necessity of the reexamination has not been made, the sample rack is stationed.

Figure 3:
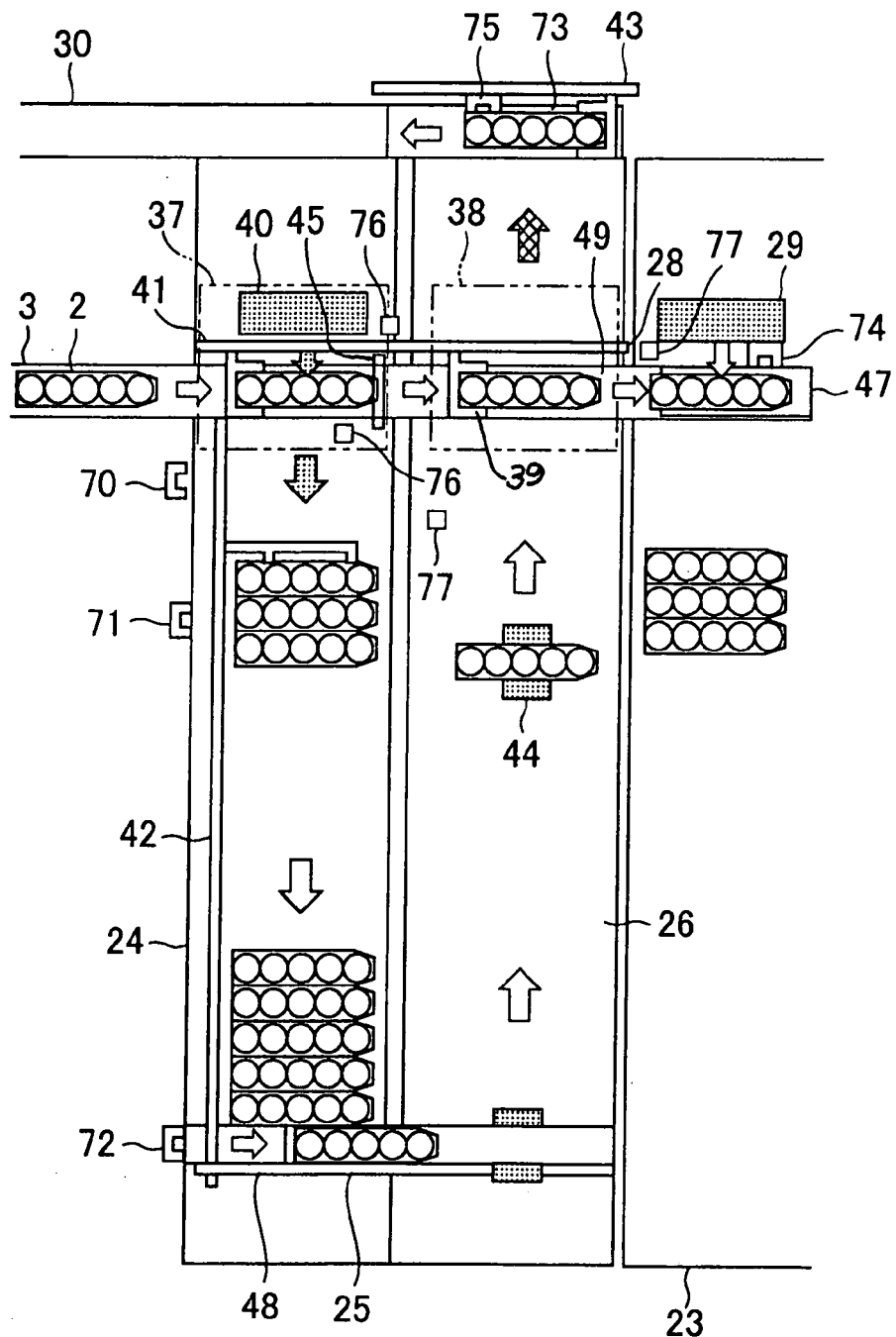
FIG. 3 is an illustration of a path of transfer of sample racks implemented in an automatic analyzing apparatuses of the first aspect of the present invention, in different modes of operation thereof.

FIG. 3 shows an automatic analyzing apparatus which is a modification of the apparatus shown in FIG. 1, wherein a pair of rack sorting mechanisms are provided in order to achieve more efficient forwarding of the sample rack to be reexamined to the return line.

The sample racks that have undergone the measurement in the analysis section includes sample racks 2 which are still awaiting the determination to be done by the control section 33 as to the necessity of the reexamination. The retractable rack stopper 45 in a first rack sorting mechanism 37 is activated, and the sample racks which are awaiting the determination are moved to the rack stationing section 24 by the operation of the rack pushing mechanism 40. Among these racks stationed in the rack stationing section 24 and waiting for the determination, a sample rack which is then determined by the control section 33 as necessitating the reexamination is transferred to the forwarding line 26 along the route which was described before in connection with FIG. 2. This sample rack 2 is then grasped by the rack forwarding arm 44 and forwarded along the forwarding line so as to be delivered from the outlet 49 of the forwarding line to the inlet 73 of the return line. The sample rack 2 is then horizontally pushed by the rack feeding mechanism 43 onto the return line 30 and is transfered by the endless belt of the return line 30 to the outlet of the return line 30, so as to be delivered to the analysis section.

Conversely, a sample rack 2 among the racks 2 stationed in the rack stationing section 24, on which the control section 33 then determines that the reexamination is unnecessary, is forwarded from the forwarding line 26 to the outlet 49 of the forwarding line by the forwarding arm 44. This sample rack 2 is then horizontally pushed by the rack take-up mechanism 28 onto the accommodation line 47 and is further pushed by the rack pushing mechanism 29 so as to be accommodated by the rack accommodation section 23.

Meanwhile, a sample rack 2, which has already been determined as necessitating the reexamination, is horizontally transfered from the first rack sorting mechanism 37 directly to a second rack sorting mechanism 38, by the operation of the rack feeding mechanism 41. A rack feeding mechanism 39 pushes the trailing end of this sample rack 2 so as to horizontally move this sample rack 2 to a position confronting the outlet 49 of the forwarding line 26. In the meantime, the forwarding arm 44 has been moved to the position confronting the outlet 49 of the forwarding line. The sample rack 2 is then forwarded from this position to the inlet 73 of the return line. The rack return mechanisim 43 pushes the head of the sample rack 2 so as to move the latter onto the transfer belt of the return line 30. The sample rack 2 is then transfered by the transfer belt to the outlet of the return line, and is delivered to the analysis unit for the reexamination.

Among the sample racks that have been sent from the first rack sorting mechanism 37 to the second rack sorting mechanism 38, a sample rack 2 on which the control section 33 has determined that the reexamination is unnecessary is horizontally pushed by the rack feeding mechanism 39 onto the accommodation line 47, and is further pushed by the rack pushing mechanism 29 into the rack accommodation section 23 so as to be stored in this section 23.

The rack sensor 74, 75, 76 and 77 are operative to detect arrival of each sample rack 2 at proper transfer position, as well as presence or absence of the sample rack at proper position.

Figure 4:
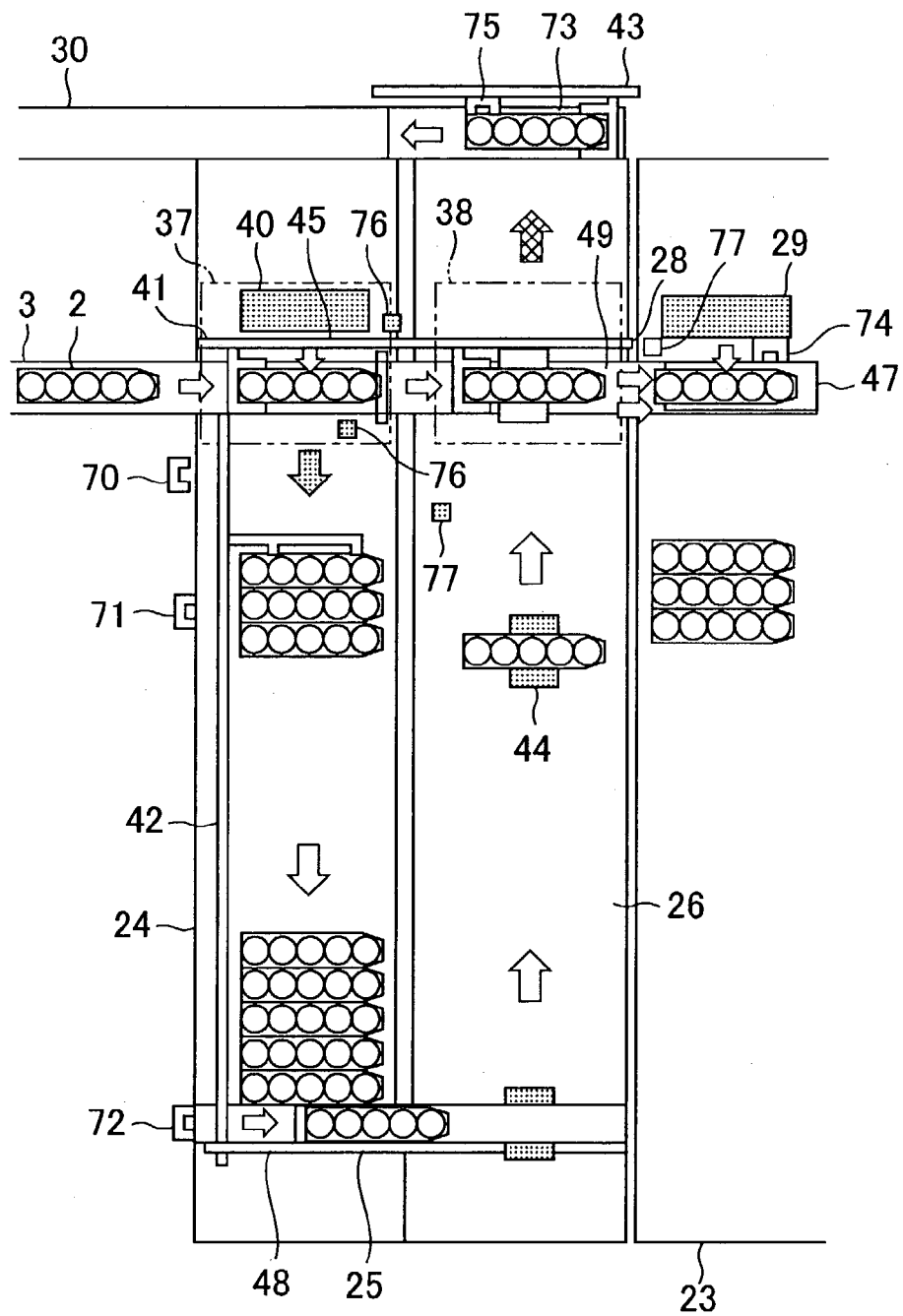
FIG. 4 is an illustration of a path of transfer of sample racks implemented in an automatic analyzing apparatuses of the second aspect of the present invention, in different modes of operation thereof.

FIG. 4 shows an arrangement which employs a pair of rack sorting mechanisms as in the case of the automatic analyzing apparatus of FIG. 3, and offers more efficient storage of the sample racks in the rack accommodation section than done by the arrangement shown in FIG. 3.

In the arrangement shown in FIG. 4, the same method of transfer as that described before in connection with FIG. 3 applies both to the sample racks which are awaiting reexamination and the sample racks which have been determined as necessitating the reexamination. However, the sample rack 2 which has been determined as not necessitating reexamination is horizontally fed by the rack feeding mechanism 41, directly from the first rack sorting section to the accommodation line 47, skipping over the rack stationing section 24 and the second rack sorting section. The sample rack 2 is then pushed by the rack pushing mechanism 29 into the accommodation section 23, so as to be stored in the latter.

Figure 5:
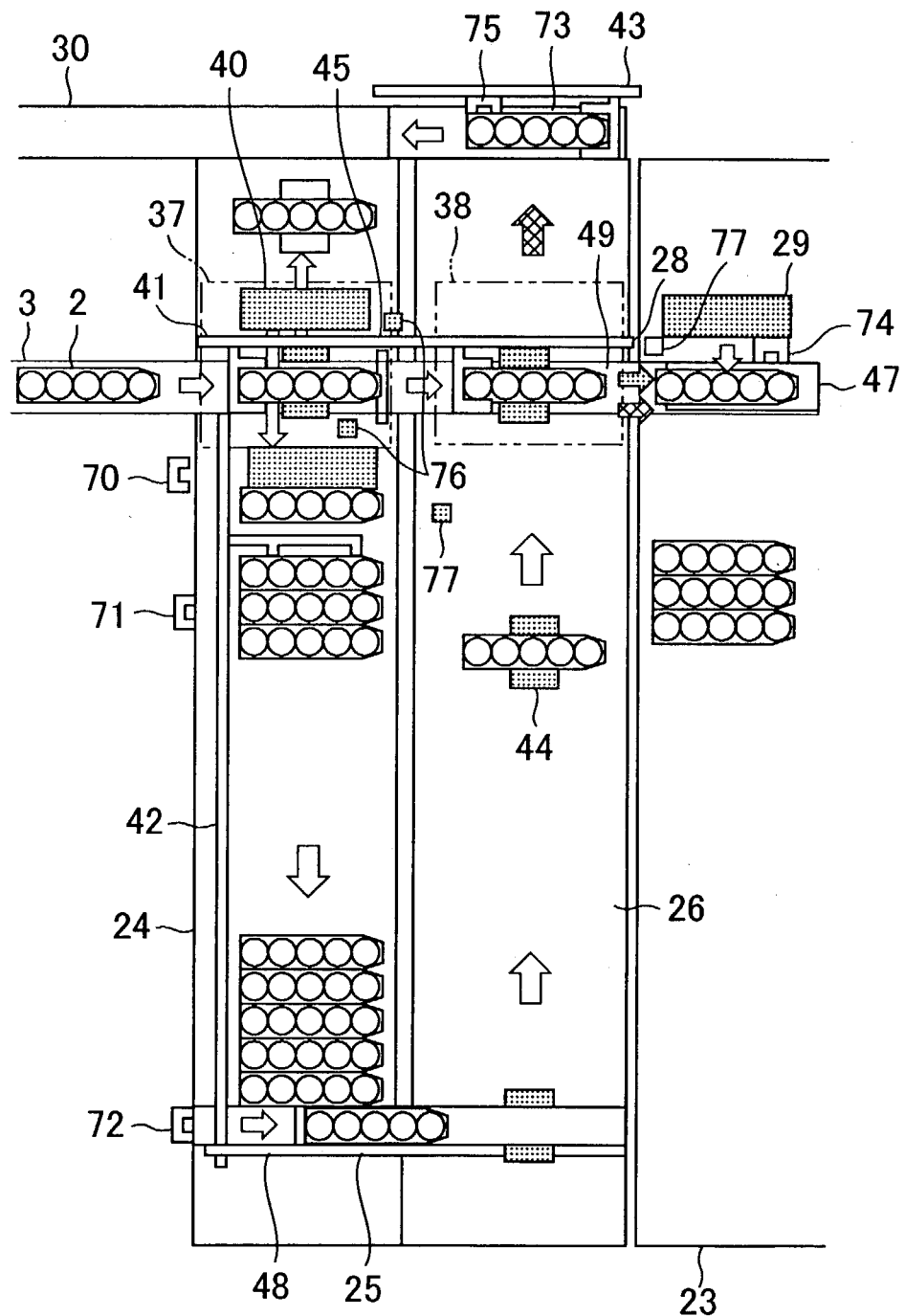
FIG. 5 is an illustration of a path of transfer of sample racks implemented in an automatic analyzing apparatuses-of the third aspect of the present invention, in different modes of operation thereof.

FIG. 5 shows an arrangement which employs a pair of rack sorting mechanisms as in the cases of the arrangements shown in FIGS. 3 and 4, and which enables forwarding of the sample racks directly to the return line by the cooperation of these rack sorting mechanisms.

Upon reaching the first rack sorting section 37, a sample rack 2 which has already been determined as necessitating the reexamination is directly fed to the return line 30 by the operation of the rack feeding mechanism 41 of the first rack sorting mechanism 37. Thus, the sample rack 2 need not be sent to the second rack sorting mechanism 38, whereby a quicker forwarding of the sample rack to the return line is implemented. In this arrangement, the sample racks 2 which are awaiting the determination as to the necessity of reexamination are handled and transfered in the same way as that described before in connection with FIGS. 2, 3 and 4. The method of transfer of the sample racks determined as not necessitating the reexamination is the same as that described before with reference to FIG. 4.

Each of the automatic analyzing apparatuses described in connection with FIGS. 3 to 5, as well as the apparatus shown in FIG. 1, can be used in such a way that a biochemical analysis is performed following an immunity analysis. In such a case, the sample racks are transfered along the same route or path as that used for the transfer of the sample racks necessitating reexamination in the apparatuses heretofore described. More specifically, instruction information that a sample rack 2 is to be subjected both to the immunity analysis and the biochemical analysis has already been recorded in a medium, by the time the sample rack 2 enters into the rack supplying section 1. In accordance with this instruction information, the control section 33 produces instructions so that the sample rack 2 with which the immunity analysis has been finished is forwarded to the biochemical analysis section. More specifically, the sample rack 2, which has undergone the measurement in the immunity automatic analysis section 14 and which is to be sent to the biochemical automatic analysis section 6, is transferred to the first rack sorting mechanism 37 through the transfer line 3. The sample rack 2 is then transferred to the return line, along a path which is the same as that tracked in the arrangements shown in FIGS. 3 to 5 by the sample rack 2 that has been determined as necessitating reexamination before arriving at the first sorting mechanism. The sample rack 2 is then transferred to the automatic biochemical analysis section 6 along the route which is the same as that described before.

According to the present invention described in claim 1, it is possible to efficiently transfer the sample racks which await determination as to the necessity of reexamination, as well as the samples that need reexamination and the samples that do not need the reexamination, by virtue of the cooperation of the pair of rack sorting sections.

According to the invention described in claim 2, an advantage in that the sample racks can be transferred from the upstream rack sorting mechanism directly to the rack accommodation line, thus achieving more efficient storage of the sample racks.

According to the invention described in claim 3, an advantage in that the sample racks can be transferred from the upstream rack sorting mechanism directly to the return line, thus achieving more efficient reexamination of the samples.

According to the present invention described in claim 4, it is permitted the samples after the immunity analysis to be quickly sent for the subsequent biochemical analysis through the return line while skipping over the stationing section, thus contributing to the shortening of the total analytic processing time.

What is claimed is:

1. An automatic analyzing apparatus, comprising:
a control section operatively connected so as to control operations of the analyzing apparatus;
a transfer line for transferring sample racks;
an analysis section, connected to said transfer line by a rack pickup mechanism, for receiving sample racks from said transfer line and examining samples extracted from sample vessels accommodated in said sample racks;
rack ejection means in said analysis section connected to said transfer line for transferring said sample racks from said analysis section back to said transfer line after extraction of said samples;
a rack stationing section connected to said transfer line downstream from said analysis section for stationing sample racks which have a possibility of being subjected to a reexamination;
a rack collecting section connected to said rack stationing section for accommodating the sample racks with which the examination has been finished;
a return line along which the sample racks that need to be reexamined are returned back to said analysis section, said return line having an inlet for receiving the sample racks from said rack stationing section;
a first rack sorting section located downstream from an outlet of said transfer line for receiving said sample racks transferred by said transfer line, said first rack sorting section being connected to said rack stationing section and directing sample racks that have to await determination as to the necessity for reexamination, to said rack stationing section, while directing sample racks that need reexamination, directly to a second rack sorting section connected to said first rack sorting section downstream therefrom by a rack feeding mechanism, said second rack sorting section being connected to an inlet of said return line and to said rack collecting section;
wherein said second rack sorting section selects, from among the sample racks which have been received from said first rack sorting section, a sample rack determined as necessitating the reexamination and directs the selected sample rack to said inlet of said return line for return to said analysis section, said second rack sorting section also directing a sample rack that has finished examination to said rack collecting section.

2. An automatic analyzing apparatus, comprising:
a control section operatively connected so as to control operations of the analyzing apparatus;
a transfer line for transferring said sample racks;
an analysis section, connected to said transfer line by a rack pickup mechanism, for receiving sample racks from said transfer line and examining samples extracted from sample vessels accommodated in said sample racks;
rack ejection means in said analysis section connected to said transfer line for transferring said sample racks from said analysis section back to said transfer line after extraction of said samples;
a rack stationing section connected to said transfer line downstream from said analysis section for stationing sample racks which have a possibility of being subjected to a reexamination;
a rack collecting section connected to said rack stationing section for accommodating the sample racks with which the examination has been finished;
a return line along which the sample racks that need to be reexamined are returned back to said analysis section, said return line having an inlet for receiving the sample racks from said rack stationing section;
a first rack sorting section located downstream from an outlet of said transfer line for receiving said sample racks transfered by said transfer line, said first rack sorting section being connected to said rack stationing section and directing sample racks that have to await determination as to the necessity for reexamination, to said rack stationing section, and selecting, from among the sample racks that need not await the determination, sample racks that do not need reexamination and directing the selected sample racks to said rack collecting section, while directing the sample racks that need the reexamination to a second rack sorting section connected to said first rack sorting section downstream therefrom, said second rack sorting section being connected to an inlet of said return line and to said rack collecting section;

wherein said second rack sorting section directs the sample racks that need reexamination received from said first rack sorting section, to said inlet of said return line for return to said analysis section, said second rack sorting section also selecting, from among the sample racks stationed in said stationing section, sample racks that need reexamination and directing the selected sample racks to said inlet of said return line for return to said analysis section, while directing the sample racks that have finished examination to said rack collecting section.

3. An automatic analyzing apparatus, comprising:

a control section operatively connected so as to control operations of the analyzing apparatus;

a transfer line for transferring sample racks;

an analysis section, connected to said transfer line by a rack pickup mechanism, for receiving sample racks from said transfer line and examining samples extracted from sample vessels accommodated in said sample racks;

rack ejection means in said analysis section connected to said transfer line for transferring said sample racks from said analysis section back to said transfer line after extraction of said samples;

a rack stationing section connected to said transfer line downstream from said analysis section for stationing sample racks which have a possibility of being subjected to a reexamination;

a rack collecting section connected to said rack stationing section for accommodating the sample racks with which the examination has been finished;

a return line along which the sample racks that need to be reexamined are returned back to said analysis section, said return line having an inlet for receiving sample racks;

a first rack sorting section downstream from an outlet of said transfer line for receiving said sample racks transferred by said transfer line, said first rack sorting section directing sample racks that have to await determination as to the necessity for the reexamination to said rack stationing section, while directing sample racks that need reexamination directly to said inlet of said return line for return to said analysis section and directing sample racks that do not need the reexamination to said rack collecting section; and a second rack sorting section connected to said first rack sorting section and said rack stationing section for selecting, from among the sample racks stationed in said rack stationing section, sample racks that need reexamination and directing the selected sample racks to said inlet of said return line for return to said analysis section, while directing the sample racks that have finished examination to said rack collecting section.

4. An automatic analyzing apparatus according to claim 1, wherein said rack stationing section has a receiving area for receiving the sample racks from an inlet of said rack stationing section and a delivery area through which said sample racks are delivered to an outlet of said rack stationing section after lapse of a stationing period, said receiving area and said delivery area being arranged to provide a substantially U-shaped path of transfer of said sample racks.

* * * * *